United States Patent [19]

Walters

[11] Patent Number: 4,606,227
[45] Date of Patent: Aug. 19, 1986

[54] APPARATUS AND METHOD FOR SIMULATING DIAGENESIS

[75] Inventor: John P. Walters, Bartlesville, Okla.

[73] Assignee: Phillips Petroleum Company, Bartlesville, Okla.

[21] Appl. No.: 703,787

[22] Filed: Feb. 21, 1985

[51] Int. Cl.[4] .......................................... G01N 15/00
[52] U.S. Cl. ............................................... 73/432 SD
[58] Field of Search .................. 73/37.8, 38, 49.8, 19, 73/432 SD, 432 J; 436/31, 28; 250/255

[56] References Cited

U.S. PATENT DOCUMENTS

| | | | |
|---|---|---|---|
| 966,078 | 8/1910 | Bowman | 73/38 |
| 2,504,143 | 4/1950 | Moore | 73/15 |
| 2,705,418 | 4/1955 | Reichertz et al. | 73/38 |
| 2,772,951 | 12/1956 | Bond | 23/230 |
| 3,162,037 | 12/1964 | Hurst | 73/38 |
| 4,093,420 | 6/1978 | Grayson et al. | 23/230 EP |
| 4,233,840 | 11/1980 | Goss et al. | 73/153 |
| 4,263,509 | 4/1981 | Fertl et al. | 250/255 |
| 4,304,122 | 12/1981 | Tentor | 73/432 SD |
| 4,355,535 | 10/1982 | Vaughan | 73/37.8 |
| 4,543,821 | 10/1985 | Davis, Jr. | 73/38 |

OTHER PUBLICATIONS

Potter, Jared Michael, "Experimental Rock-Water Interactions at Temperatures to 300° C. . . . ", Stanford University, 1981, pp. 73, 77, 78.

Charles, Robert W., "Experimental Alteration of a Granodiorite in a Circulation System", Geothermal Resources Council, Transactions, vol. 2, Jul. 1978.

Dibble, Walter E., "Study of Porosity Reduction in Sandstone", Petrophysical Services, Inc., Apr. 1982-- Mar. 1985.

Pohl, D. C., and Liou, L. G., "Flow Through Reaction of Basalt Glass . . . ", Extended Abstracts, 4th International Symposium on Water Rock Interaction, Aug.-Sep. 1983, pp. 389-392.

"International Association of Geochemistry and Cosmochemistry and Alberta Research Council", 3rd International Symposium on Water-Rock Interaction, Jul. 1980, pp. 1-213.

Primary Examiner—Stewart J. Levy
Assistant Examiner—Robert R. Raevis
Attorney, Agent, or Firm—French and Doescher

[57] ABSTRACT

An apparatus and method for simulating diagenetic models, comprising passing a fluid from a fluid supply vessel sequentially through two rock sample containment vessels, each containing a rock sample. The dual-stage, flow-through apparatus will simulate temperatures, lithostatic and hydrostatic pressures, mineralogy, fluid flow and chemistry of subsurface geologic environments.

19 Claims, 3 Drawing Figures

APPARATUS AND METHOD FOR SIMULATING DIAGENESIS

BACKGROUND OF THE INVENTION

The invention relates to a dual-stage, flow-through apparatus and method for simulating diagenesis. It further relates to a dual-stage, flow-through apparatus and method which has been designed and built to develop more accurate diagenetic models. The dual-stage, flow-through design simulates temperatures, lithostatic and hydrostatic pressures, mineralogy, fluid flow and chemistry of subsurface geologic environments.

As known sources of oil, natural gas and minerals become depleted, it is essential that these resources be replaced as efficiently and economically as possible. One means of increasing production of resources is to prepare a diagenetic history of a given rock formation prior to drilling or mining so as to determine whether that formation was subject to conditions conducive to the formation of oil, natural gas or minerals.

Diagenesis includes all processes that convert sediments to rocks between the time of deposition and the onset of thermal metamorphism. Diagenetic models are used in frontier basins to predict the existence of hydrocarbons and minerals, the location of reservoirs, the types of porosity present, the occurrence of permeability-reducing factors and the location of diagenetic seals. The potential accumulation of hydrocarbons and minerals is influenced by the diagenetic history of the rock sample.

The exploration significance of the dual-stage, flow-through apparatus lies in its potential to develop more accurate diagenetic models. The apparatus is an intermediate stage between theoretical diagenetic models and actual in-situ geological environments. Its capabilities allow physical simulation of a theoretical model. It is the dual-stage, flow-through nature of the apparatus which allows simulation of diagenesis in natural systems.

As sediments are buried, heated and compacted, fluids are expelled. The chemistry of fluids are modified by water-rock interaction. The corrosive nature of aqueous fluids causes chemical alteration of both rocks and fluids. As the fluids move, they come into contact with other minerals at varying temperatures and pressures. Although the natures of the fluids are not known with accuracy, the successive stages of the experimental apparatus would allow one to mimic this process by the natural adjustment of fluid chemistry in successive stages. By duplicating downhole temperatures, pressures, fluid chemistries, mineralogies and flow regimes through compacting basins, direct simulation of a proposed diagenetic model is possible. A dual-stage, flow-through apparatus would allow the geologist to verify his diagenetic model.

A more accurate diagenetic model would help the geologist optimize drilling and mining opportunities in a given area of study.

It is thus an object of the invention to simulate diagenesis. It is a further object to utilize a dual-stage, flow-through apparatus to develop accurate diagenetic models.

Other objects, aspects and advantages of the invention will be apparent from the specification, drawings and appended claims to the invention.

SUMMARY OF THE INVENTION

In accordance with the invention, rock samples from an underground earth formation are placed in a first and second rock sample containment vessel of a dual-stage, flow-through apparatus. The design of the apparatus allows fluids to flow through a first rock sample in a first containment vessel at a desired temperature and pressure, and subsequently through a second rock sample in a second containment vessel at a second desired temperature and pressure. The containment vessels will separate the internal fluid in contact with the rock samples from the external fluid used to simulate external pressure. The pressure, temperature and fluids desired in the apparatus may vary depending on the type of diagenetic model simulated in the apparatus.

DETAILED DESCRIPTION OF THE INVENTION

Figure 1:
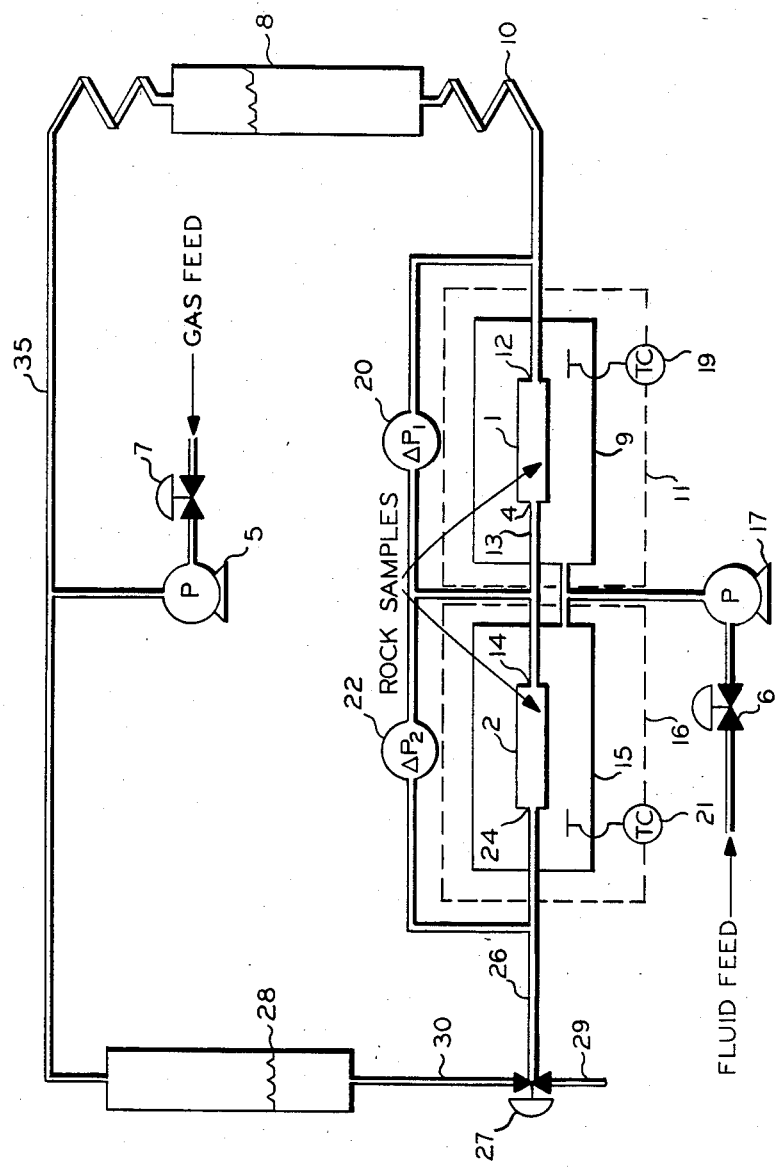
FIG. 1 is a schematic representation of a dual-stage, flow-through apparatus in accordance with the invention.

The invention is carried out in a dual-stage, flow-through apparatus which has been designed and built to develop more accurate diagenetic models. The dual-stage, flow-through apparatus allows fluids to flow through a first rock sample in a first containment vessel at a desired temperature and pressure, and subsequently through a second rock sample in a second containment vessel at a second desired temperature and pressure.

The rock samples used in the dual-stage, flow-through apparatus may vary depending upon the model proposed to simulate a geological environment. The rock samples used in the dual-stage, flow-through apparatus may be comprised of either loose aggregates of mineral grains or a natural core. The diameter and length of the rock samples may vary depending on the size of the containment vessels used in the dual-stage, flow-through apparatus. For example, in one embodiment of the invention, the rock samples may vary in size from a diameter of $\frac{1}{4}$ inch to a diameter greater than 4 inches, with the length of the rock samples being from 1 inch to greater than 8 inches. The sample size preferred for one constructed version of the invention includes a diameter of $\frac{3}{4}$ inch and a length of about 8 inches.

The invention may use an internal fluid compression pump in order to provide internal pressure to fluids in a fluid supply vessel. The pump may also be used to compress reactive naturally occurring gases, such as carbon dioxide and hydrogen sulfide. The reactive natural gases may be pumped to a fluid supply vessel to mix with other fluids so as to simulate underground fluids having contacted a reactive naturally occurring gas.

The fluids in the fluid supply vessel may vary depending upon the model proposed to simulate a geological environment. The fluids in the fluid supply vessel may be a natural solution such as fresh water or sea water or a solution containing dissolved minerals such as an oil field brine containing water that had reacted with rock over a long period of time such that it contains many different types of dissolved minerals.

The tubings used as a means to connect the internal fluid compression pump, fluid supply vessel, containment vessels, high pressure metering pump and fluid receiving vessel may be constructed of an inert material, for example, titanium, so that it will not react with the fluid. Other inert alloys commonly used in high-pressure, high-temperature reactions may also be used to construct the tubings. One such alloy is Hastelloy-C276.

An external fluid compression pump may be used to provide external pressure to the first and second containment vessels. Distilled water may be used as a medium for the external pressure. The distilled water will pass from the external fluid compression pump to two separate pressure vessels. Each containment vessel will be enclosed in a separate pressure vessel. The distilled water will surround the first and second containment vessels and provide a squeezing force on the longitudinal walls of the first and second containment vessels. The external pressure will force the walls of the containment vessels to constrict and cover the rock samples so that fluids flowing into the containment vessels will pass through the rock samples instead of around the rock samples. The external pressure will simulate the natural lithostatic pressure on the rock samples. The separate pressure vessels may be heated by a heating device so as to control the temperatures in the first and second containment vessels to any desired value. A heating device, such as a furnace, which provides a uniform temperature environment around the separate pressure vessels and first and second containment vessels will be adequate. The temperatures in the first and second containment vessel may be maintained at that value desired to simulate a geological environment.

In general, the temperatures in the first and second containment vessels will be in the range from room temperature to greater than 285° C. A temperature range of 50° C. to 200° C. is sufficient to study most reactions. The range of temperatures can be significantly increased by using materials in the construction of the dual-stage, flow-through apparatus which can withstand temperatures greater than 285° C.

A differential pressure drop across the first and second containment vessels, as fluid flows through the rock sample, is used to measure rock sample permeability. The differential pressure drop may change as a function of time as minerals dissolve and the permeability increases thus causing a decrease in the differential pressure drop.

The internal fluid pressure in the first containment vessel may be as high as 20,000 psi. The use of thin walled titanium tubing may restrict the use of higher pressures. However, it would be possible to substitute the titanium tubing with a thicker walled tubing such as Hastelloy-C 276 which would allow greater internal pressures to be used to simulate a deeper geological environment. An internal fluid pressure of 2500 psi should be sufficient to detail most internal pressures in the apparatus. This of course could vary depending on the simulated pressure of the geological environment.

The external pressure on the containment vessels must be greater than the internal pressure provided by the fluid flowing through the first and second containment vessel so that the longitudinal walls of the first and second containment vessels will adequately constrict around the rock sample. While in general any suitable external pressure may be employed, in a particular embodiment, the maximum pressure which may be used is 4500 psi, due to pressure limitations of the temperature sensor in the pressure vessel. A minor redesign of the particular pressure vessel would allow the external pressure to be increased to 8000 psi if needed, which is the maximum pressure wich can be used in a pressure vessel of this type constructed of stainless steel. It is also possible to replace the stainless steel pressure vessel with an alloy capable of operating at pressures greater than 8000 psi or to increase the thickness of the walls of the pressure vessel if needed to simulate a geological environment. External pressure of 20,000 psi may be needed to properly evaluate potential oil and mineral reserves at depths of 20,000 feet. An external pressure of 3500 psi will be sufficient in most external pressure simulations.

The residence time for fluids flowing from the fluid supply vessel through the first and second containment vessels may be any suitable value, but in general will range from a few minutes to many days depending on the simulated geological environment. Fluids from the fluid supply vessel will continually pass into the first containment vessel at a suitable flow rate. The type of fluids entering the first containment vessel may be varied depending on the simulated geological environment. It may also be appropriate to stop the fluid flow in the first containment vessel in order to form a static environment so as to study the effects of a static environment on rock samples.

The fluids in the first containment vessel will subsequently pass into a second containment vessel by means of connecting tubing. The fluids will remain in the first containment vessel for that period of time needed to simulate a geological environment before being subsequently passed into the second containment vessel.

As per the first containment vessel, the second containment vessel will be enclosed in a pressure vessel and heated by means of a heating device. The temperature in the second containment vessel is usually maintained at a lower temperature than that of the first containment vessel, since in most circulation patterns fluids will raise from a lower portion of a reservoir to a higher portion of a reservoir and thereby exhibit cooling effects. The temperature in the second containment vessel may be higher than or identical to that of the first containment vessel if such is needed to simulate a geological environment.

In the second containment vessel the flow rate of the internal fluids under most conditions will be identical to that in the first containment vessel. The residence time of the internal fluids in the second containment vessel may vary, depending on size of the rock sample and the simulated geological environment.

Under most circumstances the internal and external pressure ranges of the second containment vessel will be identical to that of the first containment vessel. However, it is possible to add additional pumps to the invention which would change the internal pressure significantly in the second containment vessel if this was desired. The pressure drop across the rock sample in the second containment vessel will vary depending on the tightness of the rock sample. A porus sample will have a low pressure drop while a tight sample such as limestone or shale will have a large pressure drop due to the relative permeability of the sample.

Internal fluid flow in the invention is caused by any suitable means, for example, by a difference between the fluid levels in the fluid supply vessel and a fluid receiving vessel. Internal fluid flow rate can be controlled by a steady lifting of the fluid supply vessel. Sampling of the internal fluid is possible between the first and second containment vessels as well as at the outlet of the second containment vessel. It is also possible to cause fluid flow by using a high pressure metering pump which would allow fluids flowing into the containment vessel to pass through the rock sample instead of around the rock sample at a controlled rate by lowering the downstream pressure in the apparatus. This would improve sampling of the fluids and allow fluids to flow through very tight rock samples in the first and second containment vessels.

Referring to FIG. 1, a first rock sample is placed in containment vessel 1 and a second rock sample is placed in containment vessel 2. Fluids from a fluid supply vessel 8 are discharged through line 10 to the internal fluid inlet 12 of containment vessel 1. The internal fluid compression pump 5 provides the internal pressure by means of tubing 35 to the fluids in the fluid supply vessel 8 which come in contact with the rock sample contained in containment vessel 1 and the rock sample contained in containment vessel 2. The internal fluid compression pump 5 by means of a valve 7 and tubing 35 allows the introduction of gases such as carbon dioxide or hydrogen sulfide to go into solution in the fluid supply vessel so as to simulate a specified geological environment.

The containment vessel 1 is located in a first pressure vessel 9 which will exert external pressure on containment vessel 1. The external pressure in the first pressure vessel 9 is produced from an external fluid compression pump 17 which is used to increase the pressure in the first pressure vessel 9. The external fluid compression pump 17 by means of valve 6 allows the introduction of a fluid such as distilled water into pressure vessel 9 as a means to increase the external pressure. The increased external pressure in the first pressure vessel 9 will constrict the longitudinal walls of containment vessel 1 so as to cause the longitudinal walls to constrict around the rock sample contained therein. The constricted walls of containment vessel 1 will prevent fluids from the fluid supply vessel 8 from flowing around (bypassing) the rock samples.

The first pressure vessel 9 is further enclosed in a first heating device 11 which will emit heat to the first pressure vessel 9 so as to increase the temperature in containment vessel 1. The amount of heat emitted to the first pressure vessel 9 may be controlled by means of a temperature sensor 19 positioned in the first pressure vessel 9. The heating device 11 and pressure vessel 9 are used to simulate elevated temperatures and pressures as fluids flow through a rock sample in containment vessel 1.

A first differential pressure device 20 is used to measure the pressure drop across the first rock sample as internal fluids flow through the first rock sample located in containment vessel 1.

The size and configuration of the first containment vessel 1, and the flow rate of the internal fluids into the first containment vessel 1 are selected so that the internal fluids will remain in containment vessel 1 for that period of time sufficient to simulate a geological environment. The internal fluids in containment vessel 1 are subsequently passed from the internal fluids outlet 4 of containment vessel 1 by means of line 13 to the internal fluids inlet 14 of containment vessel 2.

Containment vessel 2 may contain the same type or a different type rock sample as found in containment vessel 1. The containment vessel 2 is located in a second pressure vessel 15 and will be subjected to an external pressure generated by the external fluid compression pump 17. The external fluid compression pump means of valve 6 allows the introduction of a fluid such as distilled water into pressure vessel 15 as a means to increase the external pressure. The increased pressure from the external fluid compression pump 17 will act on containment vessel 2 so as to cause the longitudinal walls of containment vessel 2 to constrict around the second rock sample so as to prevent the internal fluids from flowing around (bypassing) the second the rock sample. Second Pressure vessel 15 will be enclosed in a second heating device 16 which will emit heat to the second pressure vessel 15 so as to increase the temperature in the second containment vessel 2. The amount of heat emitted to the second pressure vessel 15 may be controlled by means of a temperature sensor 21 positioned in the second pressure vessel 15. The size and configuration of the second containment vessel 2 is selected so that internal fluids will remain in containment vessel 2 for that period of time necessary to simulate the desired geological environment. Containment vessel 2 may be provided with a second differential pressure device 22, which can be used to measure the pressure drop across the second rock sample as internal fluids flow through the second rock sample in containment vessel 2. Internal fluids from containment vessel 2 will pass from the internal fluid outlet 24 of containment vessel 2 by means of tubing 26 to a valve 27 which allows fluids to be sampled from tubing 29 or be subsequently passed by means of tubing 30 to a fluid receiving vessel 28.

Flow of the internal fluids in the apparatus can be caused by the difference in fluid levels between the fluid supply vessel 8 and the fluid receiving vessel 28. Fluid flow rate can be controlled by steadily increasing the elevation of fluid supply vessel 8.

Figure 2:
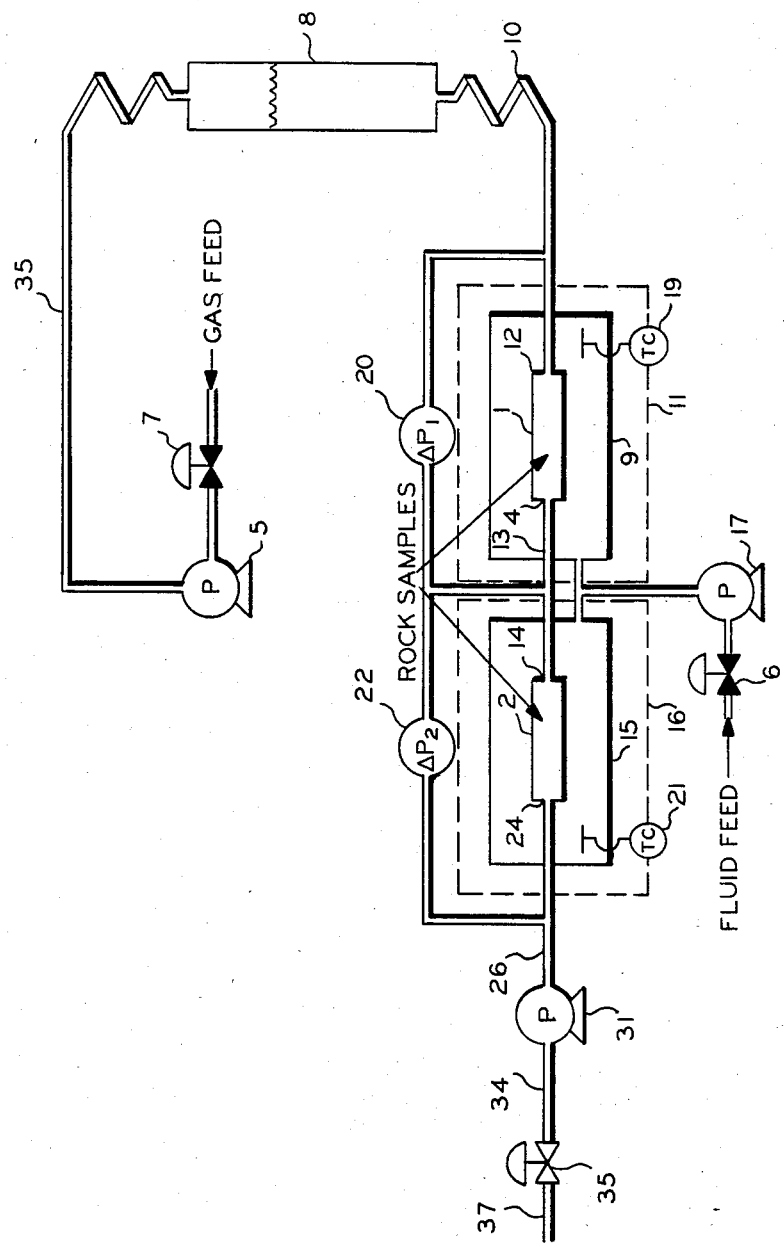
FIG. 2 is a schematic representation of a dual-stage, flow-through apparatus utilizing a high pressure metering pump in accordance with the invention.

FIG. 2 details a second embodiment of a dual-stage, flow-through apparatus utilizing a high pressure metering pump to force fluid to flow through a rock sample at a controlled rate. FIG. 2 is nearly identical to FIG. 1 except for the omission of tubing 30 and fluid receiving vessel 28 and the addition of the high pressure metering pump 31 connected by means of tubing 26 to the second containment vessel 2. The high pressure metering pump will guarantee a flow rate of fluids through the first containment vessel 1 and second containment vessel 2 by lowering the downstream pressure in the apparatus. Internal fluids from the high pressure metering pump 31 will pass by means of tubing 34 to a valve 35. Valve 35 allows fluids to be sampled by means of tubing 37.

Figure 3:
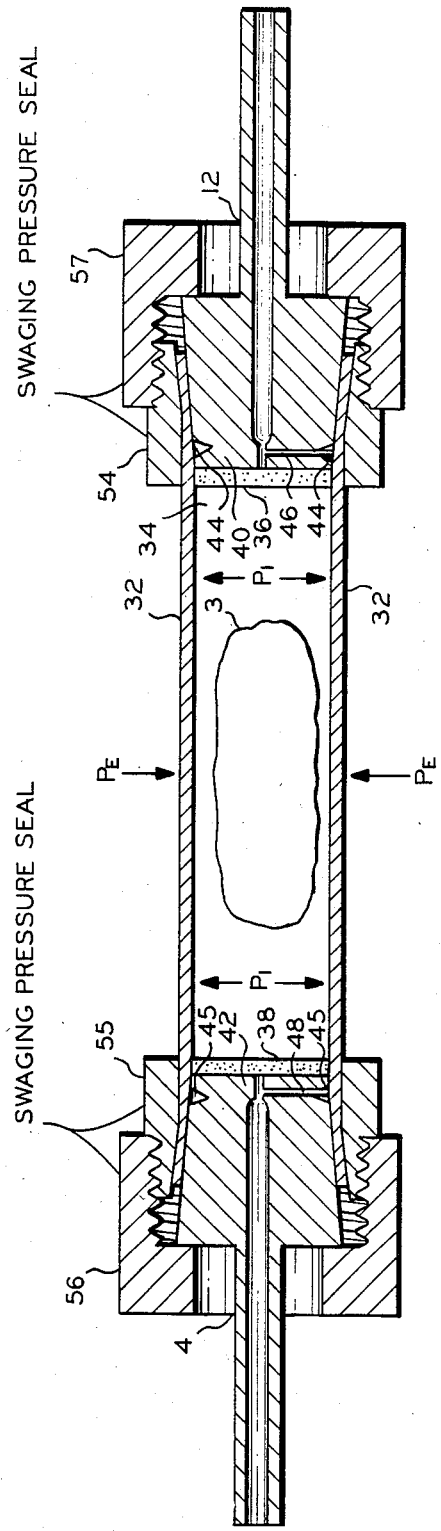
FIG. 3 is a detailed representation of a rock sample containment vessel used in the dual-stage, flow-through apparatus.

FIG. 3 details one embodiment of the containment vessels of the present invention.

All parts of the first containment vessel 1 in FIG. 3 are constructed of unalloyed titanium with the exception of a flexible polytetrafluorethylene tubing 32 which is used to isolate the external fluid at external pressure, $P_E$, from the internal fluid at internal pressure, $P_I$. The flexible polytetrafluoroethylene tubing 32 has a diameter of $\frac{3}{4}$ inch and a wall thickness of 0.030 inch. The diameter and wall thickness of the polytetrafluoroethylene tubing 32 may vary depending on the simulated geological environment and the size of the rock sample used in the sample chamber 34 formed by the flexible polytetrafluoroethylene tubing 32. The flexible polytetrafluoroethylene tubings 32 may be longitudinally alligned. The containment vessel may be constructed of other inert materials such as platinum or gold which are stronger materials and will exhibit greater resistance to excess pressure and temperature than titanium or polytetrafluoroethylene. The flexible polytetrafluoroethylene tubing 32 will here-in-after be referred to as flexible tubing.

The rock sample 3 is initially placed in the sample chamber 34 of the flexible tubing 32 prior to introduction of frits 36 and 38 and conical shaped tapered end plugs 40 and 42 at opposite ends of the flexible tubing 32. The size of the rock sample 3 may vary depending on the size of the sample chamber 34 formed by the flexible tubing 32.

Frits 36 and 38 may be constructed of centered titanium powder and may be placed at opposite ends of the flexible tubing 32. Each frit 36 and 38 is a filter used to prevent the rock sample 3 from leaving the flexible tubing 32. The porosity of frits 36 and 38 can vary depending on the particle size of the rock sample 3 contained in the sample chamber 34 of the flexible tubing 32.

Conical shaped tapered end plugs 40 and and 42 can be used at opposite ends of the flexible tubing 32 as a means to seal the flexible tubing 32 so as to prevent external fluid from leaking into the flexible tubing 32 and mixing with internal fluid. Internal fluid inlet tubing 12 can be welded to end plug 40 and internal fluid outlet tubing 4 can be welded to end plug 42, so as to allow internal fluids from the fluid supply vessel 8 to pass through end plugs 40 and 42 by means of internal fluid inlet tubing 12 and internal fluid outlet tubing 4.

A further means of ensuring a seal between the flexible tubing 32 and end plugs 40 and 42 is by means of circumferential groves 44 and 45 positioned at opposite ends of the flexible tubing 32 and in communication with the internal fluids by means of conduit 46 and 48 positioned at opposite ends of the flexible tubing 32, and a swaging pressure seal positioned at opposite ends of the flexible tubing 32.

The external pressure from the external flud squeezes the flexible tubing 32 into the circumferential groves 44 and 45 positioned at opposite ends of the flexible tubing so as to form a seal between the flexible tubing 32 and end plugs 40 and 42.

Each swaging pressure seal is comprised of collars 54 and 55 drawdown nuts 56 and 57 positioned at opposite ends of the flexible tubing 32. The drawdown nuts 56 and 57 are used to squeeze the collars 54 and 55 at opposite ends of the flexible tubing 32 so as to force the flexible tubing to contact the end plugs 40 and 42 positioned at opposite ends of the flexible tubing 32 so as to ensure a complete seal.

The external pressure on the exterior of the flexible tubing 32 will cause the flexible tubing 32 to constrict around the rock sample 3 so as to force internal fluids flowing into the flexible tubing 32 from a fluid supply vessel 8 to flow through the rock sample 3 rather than around it. This will ensure that the internal fluids come in contact with the interior of the rock sample 3 used in the flexible tubing 32. The internal fluids flowing into the flexible tubing 32 by means of an internal fluid inlet tubing 12 can remain in the flexible tubing 32 for such period of time as needed to simulate geological environment. The fluids are subsequently passed through internal fluids outlet tubing 4 to a second containment vessel 2 which may be constructed identically to containment vessel 1.

EXAMPLE I

A theoretical diagenetic model of the Smackover Formation of Southern Alabama which explains replacement of calcite, anhydrite and quartz has been experimentally verified using the dual-stage, flow-through apparatus of their invention. Experimental verification of this and other diagenetic models incorporating fluid circulation is necessary because calculated diagenetic models suffer from inaccurate thermochemical data available in the literature. Mathematical models are not yet sophisticated enough to accurately represent the geochemical properties and behavior of concentrated compositionally-complex natural brines. The experimental approach is an intermediate stage for verifying or improving theoretical models. The exploration significance of this experimental study lies in the verification of a diagenetic model of calcite dissolution with the concomitant precipitation of anhydrite and quartz.

In the Smackover Formation of Southern Alabama, large anhydrite crystals are observed with margins that cut through calcitic ooids and quartz overgrowths are observed that penetrate the margins of calcite grains. Precipitated quartz suggests cooling of quartz-saturated fluids. Calcite is known to increase in solubility as fluids cool (retrograde solubility). It is possible that calcite replacement by anhydrite could also be caused by the cooling of calcite/anhydrite-saturated fluids, although anhydrite alone also exhibits retrograde solubility.

Careful calculation of the relative sensitivities of anhydrite and calcite solubilities reveals that calcite increases in solubility more quickly in cooling fluids, under some conditions, than anhydrite. A calculation for calcite/anhydrite saturated fluids cooling from 200° C. to 50° C. estimates that under some conditions calcite solubility increases 1.3 times as fast as does anhydrite solubility. The rapid release of calcium ion from dissolving calcite overcomes the tendency of anhydrite to dissolve and anhydrite precipitates instead. The diagenetic features observed in the Smackover Formation could be caused by fluid circulation driven by geothermal anomalies created by the high thermal conductivity of salt domes. Deep fluids, equilibrated with calcite, anhydrite and quartz are driven upward by the thermal anomaly. As the fluids cool and come in contact with other sediments, calcite dissolves and is replaced by anhydrite and/or quartz. Excess calcite dissolution will create secondary porosity (i.e. potential sites for oil accumulation).

In order to verify the theoretical model, experiments were conducted in a dual-stage, flow-through apparatus with a temperature of the first rock sample containment vessel maintained at 200±1° C. and that of the second rock sample containment vessel maintained at 50±1° C. 1.00 m NaCl brine was flowed successively through the two rock sample containment vessels at 0.5 ml/hr (0.07 pore volumes/hr). The internal volume of the tubing between the two rock sample containment vessels resulted in a seven hour time lag for fluid travel between the two rock sample containment vessels. The internal pressure (PI, i.e. hydrostatic) was maintained at 1512±12 psi with 1.00 percent $CO_2$ in $N_2$ ($CO_2$ partial pressure=1.03 atmospheres). The external pressure ($P_E$, i.e. lithostatic) was maintained at 2600±100 psi. After one week of reaction, the samples were cooled, removed and inspected for signs of dissolution or precipitation. Chloride analysis of the reacted brine indicates that brine dilution from the $P_E$ fluid ($H_2O$) was less than or equal to 1 percent.

The mineral samples were crushed 16–32 mesh anhydrite, from Belmont, New York, and 16–80 mesh calcite (Iceland spar) rhombs from Creel, Chihuahua, Mexico. The anhydrite exhibited many imperfect cleavage faces, with many small adhering fragments. The calcite showed very smooth cleavage faces with numerous steps between cleavage planes and many adhering fragments.

Anhydrite and quartz in equal amounts were placed in both rock sample containment vessels. The quartz was Ottawa Sand Fisher/523 which is used as standard sand for cement testing. The quartz was used mainly as a filler for the anhydrite.

The sample from the cooler second rock sample containment vessel at 50° C. exhibited numerous dissolution features. The broken corner of the anhydrite in the rock sample containment vessel exhibited many small edges that eroded. Some etch pits were also in evidence. It was shown from the example that anhydrite saturated fluids upon cooling will dissolve anhydrite when no calcite is present.

EXAMPLE II

A second experiment was conducted in the same dual-stage, flow-through apparatus under the identical conditions as in Example I. The only difference between Example I and Example II was that calcite was added to both rock sample containment vessels 1 and 2. It was evidenced that anhydrite from the cooler second rock sample containment device at 50° C. showed clear evidence that incipient overgrowths were present. The edges of the surface features were very linear and the surfaces were very smooth. This was in contrast both to the starting material and the reacted anhydrite from the first experiment. Clearly, anhydrite/calcite saturated fluids will precipitate anhydrite upon cooling when calcite is present. Calcite from the second experiment, second rock sample containment vessel exhibited eroded cleavage steps. Deeply eroded edges and rows of etch pits with crystallographic orientation were evident. Edges with an appearance of severe "nibbling" were also found. This demonstrates that anhydrite/calcite saturated fluids will dissolve calcite as anhydrite is being precipitated.

Examples I and II clearly predict that cooling calcite/anhydrite saturated fluids will concurrently dissolve calcite while precipitating anhydrite. Cooling anhydrite saturated fluids in the absence of calcite will dissolve anhydrite. The diagenetic model of concurrent anhydrite precipitation in calcite dissolution caused by circulating cooling fluids in a Smackover Formation of Alabama was verified. The dual-stage, flow-through apparatus of the present invention was required to verify this model. The dual-stage, flow-through apparatus is an important improvement in the production of diagenetic models which include fluid circulation.

Variation and modification are possible within the scope of the invention as described herein. One skilled in the art in possession of this disclosure having studied the same will understand that various engineering details of operation are necessarily omitted for sake of simplicity.

We claim:

1. A process for simulating diagenesis, comprising:
   maintaining a first rock sample in a first sample chamber of a first containment vessel at a first temperature;
   maintaining a second rock sample in a second sample chamber of a second containment vessel at a second temperature;
   passing fluids under pressure at a controlled rate into and through said first rock sample in said first sample chamber of said first containment vessel and then passing said fluid into and through said second rock sample in said second sample chamber of said second containment vessel.

2. A process in accordance with claim 1 wherein said fluids comprise fresh water, salt water or fluids containing dissolved minerals.

3. A process in accordance with claim 1 wherein said first and second rock samples in said first and second sample chambers comprise loose aggregates of mineral grains or a core.

4. A process in accordance with claim 3 wherein each of said first and second rock samples in said first and second sample chambers are generally cylindrical with the diameter of each of said first and second rock samples being in the range of about ¼ inch to about 4 inches and the length of each of said first and second rock samples being in the range of about 1 inch to about 8 inches.

5. A process in accordance with claim 1 wherein said first and second temperatures in said first and second containment vessels are in the range of about room temperature to about 285° C. or greater.

6. A process in accordance with claim 1 wherein the internal pressures in said first and second containment vessels are in the range of about atmospheric pressure to about 20,000 psi.

7. A process in accordance with claim 1 wherein the external pressures on said first and second containment vessels are in the range of about atmospheric pressure to about 20,000 psi.

8. A process in accordance with claim 1 wherein said first containment vessel comprises a first longitudinally aligned flexible tubing and said second containment vessel comprises a second longitudinally aligned flexible tubing, said first flexible tubing forming said first sample chamber and said second flexible tubing forming said second sample chamber.

9. A process in accordance with claim 8 wherein said external pressures on said first and second containment vessels are greater than said internal pressure in said first and second containment vessels such that said external pressures on said flexible tubings of said first and second containment vessels will cause said flexible tubings of said first and second containment vessel to constrict around said first and second rock samples, so as to allow said fluids flowing into said first and second sample chambers to flow through said first and second rock samples in said first and second sample chambers instead of around said first and second rock samples.

10. A process in accordance with claim 1 wherein said first and second containment vessel which comes in contact with said fluids are comprised of inert materials.

11. A process in accordance with claim 1 wherein said fluids will flow through said first and second rock samples in said first and second sample chamber for such period of time sufficient to simulate a geological environment.

12. An apparatus for simulating diagenesis comprising:

(a) means for supplying fluids under pressure;
(b) means for defining a first sample chamber adapted to contain a first rock sample in said first sample chamber; and a second sample chamber adapted to contain a second rock sample in said second sample chamber;
(c) means for passing fluids from said means for supplying fluids into and through said first rock sample in said first sample chamber; and then passing said fluids into and through said second rock sample in said second sample chamber;
(d) means for heating said first sample chamber so as to increase a first temperature in said first sample chamber and for heating said second sample chamber so as to increase a second temperature in said second sample chamber;
(e) means for receiving fluids passing through said second rock sample in said second sample chamber.

13. An apparatus in accordance with claim 12 wherein said means for defining said first and second sample chambers comprises a first containment vessel containing a first longitudinally aligned flexible tubing and a second containment vessel containing a second longitudinally aligned flexible tubing, the interior space of said first flexible tubing and said second flexible tubing forming said first and second sample chambers.

14. An apparatus in accordance with claim 13 wherein said first and second temperatures are in the range of about room temperature to about 285° C. or greater.

15. An apparatus in accordance with claim 13 wherein the internal pressure in said first and second sample chamber is in the range of about atmospheric pressure to about 20,000 psi.

16. An apparatus in accordance with claim 13 further comprising means for applying external pressure on said flexible tubings in the range of about atmospheric pressure to 20,000 psi.

17. An apparatus in accordance with claim 16 wherein said external pressure is greater than the internal pressure in said flexible tubings such that said external pressure on said flexible tubings will cause said flexible tubings to constrict around the longitudinal surfaces of said first and second rock samples, so as to allow said fluids flowing into said first and second sample chambers to flow through said first and second rock samples instead of around said first and second rock samples.

18. An apparatus in accordance with claim 12 wherein said apparatus which comes in contact with said fluid is comprised of inert materials.

19. An apparatus in accordance with claim 12 wherein said fluids will flow through said first and second rock samples for such period of time sufficient to simulate a geological environment.

* * * * *